United States Patent [19]

Krupka et al.

[11] 4,445,512

[45] May 1, 1984

[54] METHOD AND APPARATUS FOR EVALUATING PACER BATTERY STATUS AND STIMULATION EFFECTIVENESS

[75] Inventors: Yaakov Krupka, Rehovot; Salomon Feldman, Givatayim; Shmuel Yerushalmi, Rehovot, all of Israel

[73] Assignee: Omikron Scientific Ltd., Rehovot, Israel

[21] Appl. No.: 408,742

[22] Filed: Aug. 17, 1982

Related U.S. Application Data

[63] Continuation of Ser. No. 123,045, Feb. 20, 1980, abandoned.

[30] Foreign Application Priority Data

Feb. 20, 1979 [IL] Israel .................................... 56700

[51] Int. Cl.³ .............................................. A61N 1/36
[52] U.S. Cl. ............................................. 128/419 PT
[58] Field of Search .................. 128/419 PG, 419 PT

[56] References Cited

U.S. PATENT DOCUMENTS

| | | | |
|---|---|---|---|
| 3,669,120 | 6/1972 | Nielsen .......................... | 128/419 PG |
| 3,718,909 | 2/1973 | Greatbatch ..................... | 128/419 PT |
| 3,783,878 | 1/1974 | Thaler et al. .................. | 128/419 PT |
| 3,837,348 | 9/1974 | Thaler ........................... | 128/419 PT |
| 3,939,844 | 2/1976 | Pequignot ...................... | 128/419 PG |
| 4,041,954 | 8/1977 | Ohara ............................ | 128/419 PT |

*Primary Examiner*—William E. Kamm
*Attorney, Agent, or Firm*—Fleit, Jacobson, Cohn & Price

[57] ABSTRACT

A pacemaker of the inhibited demand type which is equipped with a battery and pacemaker efficiency evaluator. A magnetically initialized test circuit synchronizes the timing of test stimulating pulses with the natural R-wave or, the end of a basic pacemaker escape interval, thereby to enhance patient safety by avoiding competition during testing. The synchronized test circuit produces an alternating sequence of sensing and pacing periods which are maintained during the test. Upon actuation of the test, the first R-wave, or the end of the basic pacer interval, is sensed and a number of stimulating pulses is applied at the end of successive test intervals, which intervals are located between pacemaker output pulses, the duration of which indicates the battery status. This sequence of sensing, synchronization, an application of test pulses is repeated during the duration of the magnet test.

3 Claims, 3 Drawing Figures

METHOD AND APPARATUS FOR EVALUATING PACER BATTERY STATUS AND STIMULATION EFFECTIVENESS

This is a continuation of application Ser. No. 123,045 filed Feb. 20, 1980 now abandoned.

FIELD OF THE INVENTION

The present invention relates to heart stimulating devices, and more particularly to implantable inhibited types.

BACKGROUND OF THE INVENTION

Standby or demand or inhibited or synchronized type cardiac pacemakers are provided with means to convert the standby or sensing state to a fixed predeterminated pacing rate mode which allows several tests of the pacer to be performed, and of its system, such as tests of the cell or battery voltage, which is indicated by the deviation in the testing rate or/and stimulating spike width; the stimulation threshold; the electrode system malfunctions; and other parameteric measurements. This fixed predetermine testing rate induces competition between the cardiac spontaneous rhythm and the pacer stimulating rate.

This competition may develop a spike-on-T phenomenon, this latter being known as a cardiac vulnerable period, and this may be dangerous in case of active coronary insufficiency. The object of this invention is to reduce this danger by introducing synchronization of the fixed testing rate with the spontaneous cardiac rhythm.

Additionally, there is a need for heart stimulation in order to terminate tachyarrhythmias by reverting to normal sinus rhythm. Today this is done by stimulating the heart with high frequency electrical spikes until the desired conversion occurs. Application of the hereby disclosed synchronization system carries the stimulation spike into the diastole period, thus, terminating the tachyarrhythmias more efficiently and without the danger of overstimulation.

According to a further feature of the present invention, means are provided for terminating tachyarrhythmias, in patients with implanted demand or other pacemakers, and this is accomplished by means of application of heart stimulation at a predetermined higher frequency. According to a preferred embodiment, means are provided for applying a stimulating spike for terminating such cardiac tachyarrhythmias, said spike being applied into the diastolic period, and means for repeating such stimulating spikes, as required, synchronized with the heart beat rate, and for repeating such stimulation at predetermined intervals.

The novel device is based on conventional circuitry, and preferable on C-MOS technology logic circuits which exert a low current drain on the energy source. Linear circuit means can also be used for such devices.

BRIEF DESCRIPTION OF THE DRAWINGS

The invention is illustrated in the accompanying drawings, wherein:

FIG. 4 is a typical logic solution based on C-MOS circuitry for n predetermined stimulating spikes, where n is any desired integer.

DESCRIPTION OF THE PREFERRED EMBODIMENT

Figure 1:
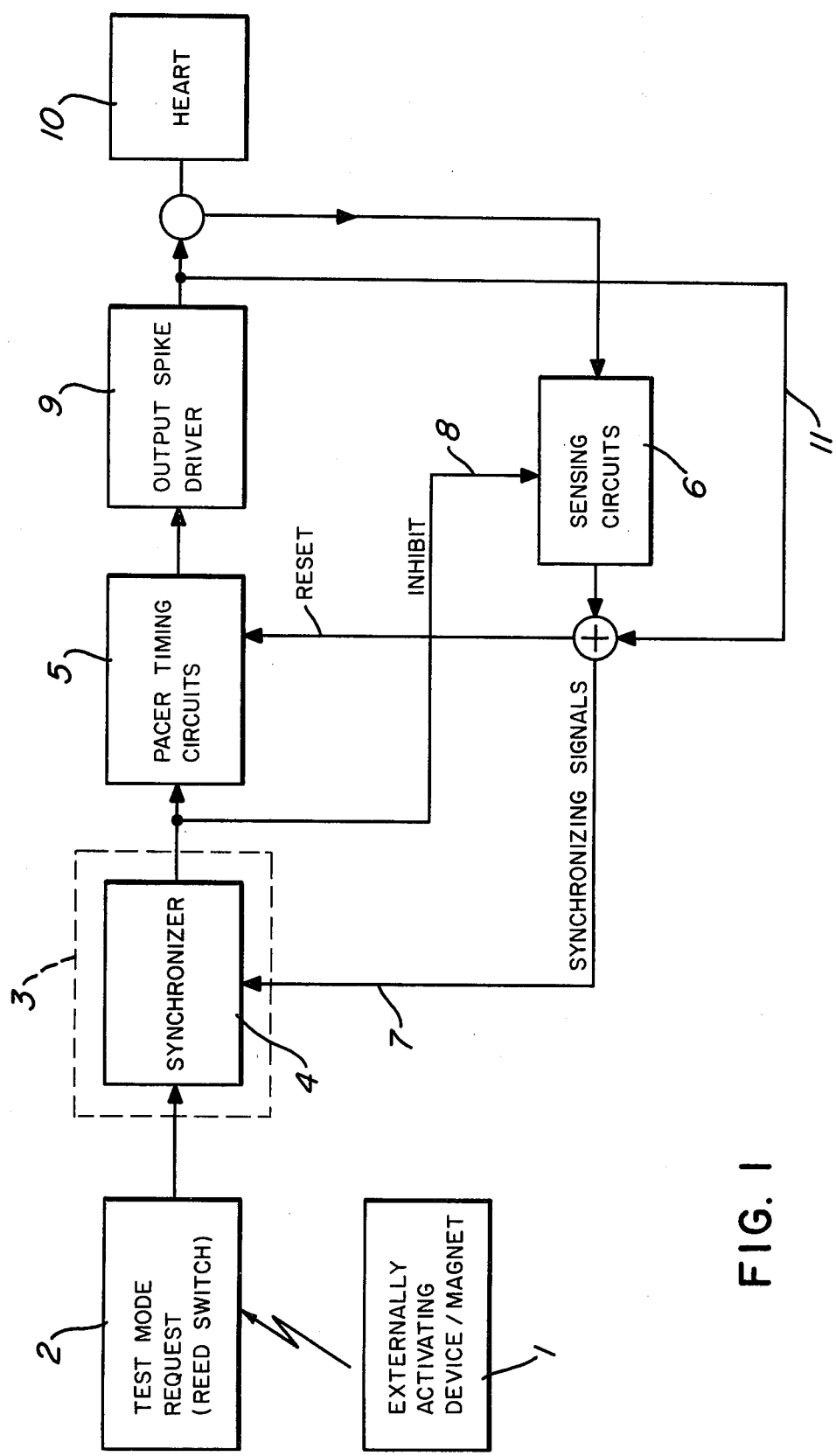
FIG. 1 is a block diagram of the typical inhibited cardiac pacer with implemented synchronizer of this invention.

FIG. 1 shows the functional block diagram of a typical cardiac inhibited pacer in combination with the synchronizer. Refering to this block diagram, 3 designates the novel synchronizer block 4 and its connections with the other functional blocks. Upon request for a testing rate mode, by means of external activating device 1 and its activating receiver 2, the synchronizer responds by sensing of synchronizing signals on line 7. These signals are of one of the following kinds: either the heart beat activity segment detected by sensing circuits 6 or stimulating spikes delivered by output spike driver 9 via line 11. The first of these signals activates the synchronizer circuits for the predetermined number of stimulating spikes, and thus the synchronizer responds by inhibiting via line 8, the sensing circuitry 6 for this period, i.e. till the predetermined number of stimulations are executed. Simultaneously, the pacer timing circuits 5 are shifted to a higher stimulating rate.

Figure 2:
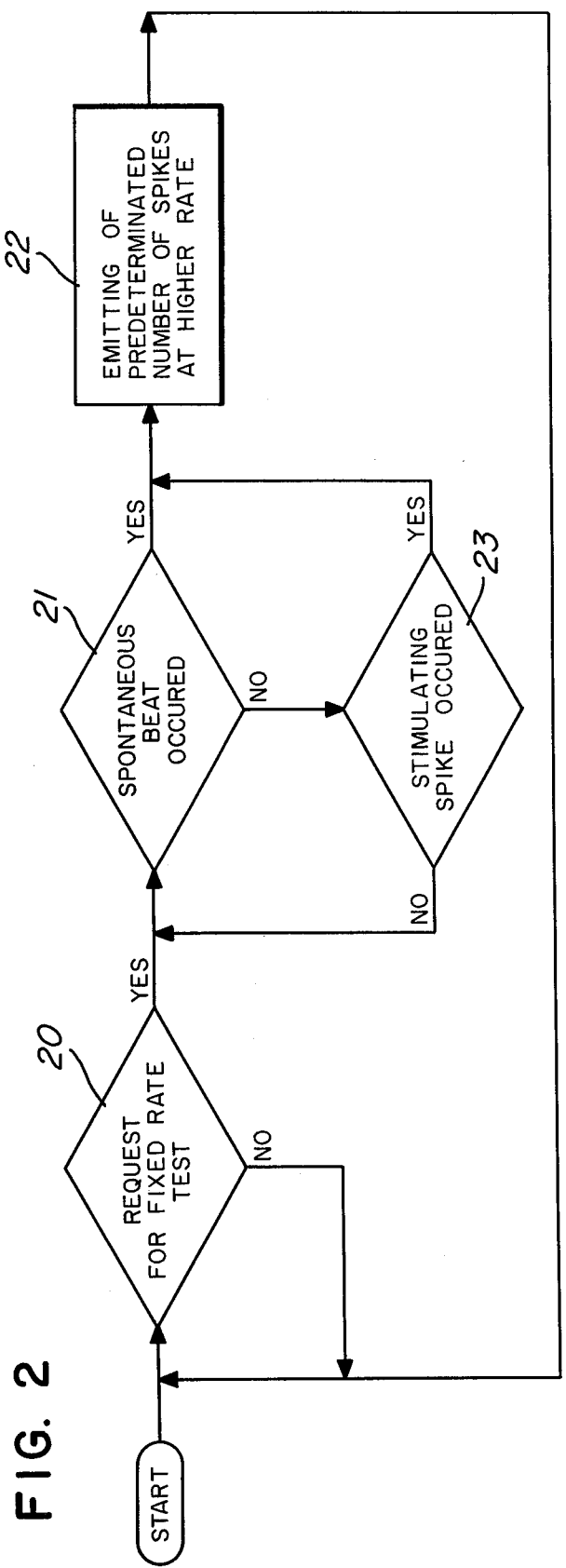
FIG. 2 is a flow diagram illustrating the signal processing of the synchronizer.

FIG. 2 shows the signal processing of the synchronizer by means of a flow diagram. Because of the details given in the diagram further description of it is omitted.

Figure 3:
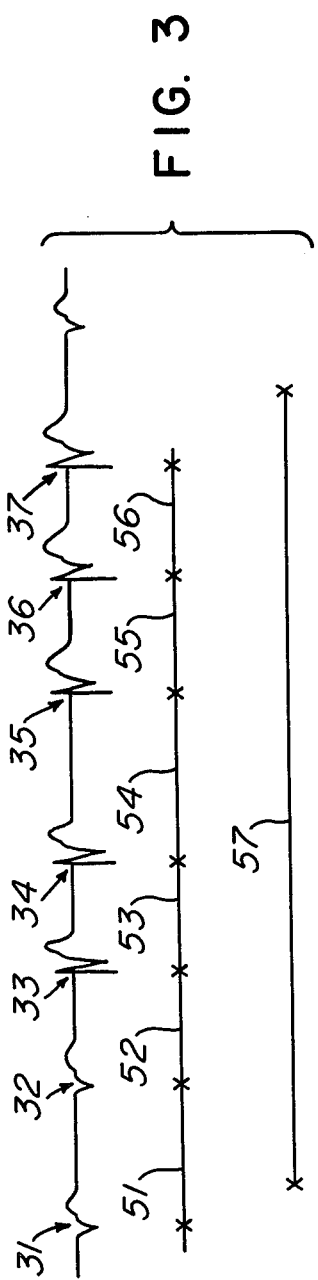
FIG. 3 is an ECG pattern illustrating the performance of the novel synchronizer in case of two predeterminated stimulating spikes. The intervals are given for reference.

FIG. 3 illustrates a typical Electrocardiogram pattern. The test duration is defined by 57. This demonstrates the synchronization of the pacing spikes of the testing rate to beat 32. The predeterminated number of fixed rate stimulation spikes was determined as two. (Here the application of stimulating spikes 33, 34, and 35 is combined into one sequential pattern.) The sequence of illustrated events is as follows:

Reference is made to FIG. 1 and FIG. 3. The interval 51 is a spontaneous R-R interval. During this interval 51, a testing rate was initiated, thus the beat 32 is the first synchronization beat upon which the synchronizer 4 inhibits sensing circuits 6 for the two stimulation intervals 52 and 53. These stimulation intervals are shorter than the pacing interval 54 and are established according to clinical requirements. The stimulating spikes 33 and 34 are generated by the pacer timing circuits 5 with the higher rate controlled by the synchronizer 4. Upon reception of the second stimulating spike 34 the synchronizer 4 cancels inhibit 8 and the sensing of the pacer is resumed. In this illustration no spontaneous beat was received during the basic stimulation interval 54 which led to application of stimulating spike 35 inherently produced by the pacer timing circuit 5. The later spike 35 convert the synchronizer for two successive intervals 55 and 56 bounded by the higher rate stimulating spikes 36 and 37. Since the request of the test mode was terminated somewhere following stimulating spike 37, the synchronizer stopped its intervention and from this point the pacer exhibits its normal sensing and pacing functions. The synchronizer can be incorporated at any suitable combination and length of period 57.

FIG. 4 illustrates an example of actual solution using standard C-MOS logic circuits. The shift register 63 is used as a counter for a predetermined number of stimulations during fixed mode test. This shift register 63 is under reset unless testing mode is requested by 64. An Inverter 65 converts a conventional low-level request signal from the request circuit 64 to a high-level logic signal, and applies the same to OR gate 66 thereby to energized it. During its reset state the output Q1, which is used as the output control line 68, is at zero and thus neither inhibit of the sensing nor increased rate is activated. Upon request of the testing mode the OR gate 66 releases reset from the shift register 63, and thus the first pulse arriving at the CL input of 63, in the form of synchronizing signals 61, sets Q1 to logic ONE. Q1 in turn activates via 68 the inhibit of pacer sensing 6 and commands a high stimulating rate of the pacer timing circuits 5. The next series of stimulating spikes will advance the shift register 63 until Qn, which is the n-1 count of the stimulating spikes, changes to logic ONE. The Qn at logic ONE substitutes logic ZERO through the invertor 62 to input D of 63, and thus the next spike received at CL will transfer Q1 to logic ZERO. This will cancel both the inhibit and increased rate control 68 and reset the whole shift register to its zero or initial position via differentiator 67 and OR gate 66. From this state the synchronizer is awaiting the synchronizing signal, upon reception of which the new cycle of synchronization is generated as described above. This will repeat as long as the testing mode is requested.

The novel pacer was evaluated on a number of patients previously equipped with demand pacemakers. When the test was actuated, the synchronizer gated the reed switch and the synchronizing signals, thus controlling the pacer timing circuits for a higher pacing rate and at the same time inhibiting the sensing circuits for two pacing intervals per synchronization cycle. Actually upon attachment of the magnet, the first R-wave or stimulator spike, which ever occurs first, converts the pacing into a test rate mode for two consecutive spikes, at, say 100 ppm rate. Thereafter pacing reverts to the sensing mode for one escape interval and again, upon occurence of R or of a stimulator spike, two spikes are emitted at the same or at another predetermined frequency. This can be repeated as long as required. Two consecutive spikes, at fixed intervals, are generally adequate in order to evaluate the pacemaker system. Twenty patients were connected temporarily to a synchronized pacemaker according to the present invention. As average of 200 synchronized tests were made per patient and recorded for evaluation. Spike on T phenomenon was detected in less than 5 percent of the periods, compared with an average of 45 percent during conventional magnet tests. Preliminary tests indicate that the novel device is efficient in terminating tachyarrhythmias in human patients.

It is clear that the novel concept of synchronization of the tests of the pacemaker with the heart rate and such synchronization during applications of stimulating spikes for terminating tachyarrhythmias can be applied to numerous types of pacemakers and similar instruments and all such applications are within the scope and spirit of the present invention.

What is claimed is:

1. A method for evaluating the battery status and stimulating effectiveness of an inhibited type cardiac pacemaker system which issues periodic stimulating pulses between basic pacemaker intervals, said pacemaker system including magnet test means for performing said evaluating in a number of magnetic test intervals, means for activating said magnet test means, a synchronizer for coordinating the timing and sensing circuits of the pacemaker system, said system being capable of sensing periodic R-waves of a heart, which method comprises the step of:
    (a) applying magnetic means to actuate said magnetic test means;
    (b) sensing one of a first natural R-wave and the end of a first basic pacemaker interval;
    (c) applying a predetermined number of consecutive asynchronous stimulation pulses, said asynchronous pulses being applied after a magnetic test interval which is shorter in duration than the basic pacemaker interval;
    (d) sensing one of the next R-waves and end of a basic interval;
    (e) applying again a sequence of a predetermined number of consecutive asynchronous stimulating pulses during the magnetic test intervals; and
    (f) repeating steps (a) through (e) for the duration of the magnet test, whereby the length of the magnet interval and the heart response to the stimulating pulses being indicative of battery status and stimulation effectiveness, respectively.

2. A method as recited in claim 1, wherein a sequence of sensing periods follows two asynchronous stimulation pulses.

3. An inhibited demand pacer for applying stimulating pulses to a heart, said pacemaker including means for evaluating the status of a battery and the efficiency of stimulation, timing and sensing circuits for sensing periodic natural R-waves of the heart and for timing the application of stimulating pulses to the heart in the absence of a periodic R-wave, said pacer comprising:
    magnetic test means for performing said evaluation in response to a magnetic field during successive magnetic test intervals;
    synchronizing means for coordinating the timing and sensing circuits of the pacemaker;
    means for actuating the magnetic test means so as to sense one of a first natural R-wave of the heart and the end of a first basic timing interval between stimulating pulses;
    means for applying two or more consecutive asynchronous stimulation pulses, each at the end of a magnetic test interval which is shorter in duration than the basic timing interval;
    means for synchronizing the stimulating pulses of the pacer with one of a next natural R-wave and the end of a next basic timing interval; and
    means for repeating the stimulations during said evaluation until the end of the magnetic test period.

* * * * *